United States Patent
Aoyama et al.

(12) 
(10) Patent No.: US 6,494,077 B2
(45) Date of Patent: Dec. 17, 2002

(54) ODOR IDENTIFYING APPARATUS

(75) Inventors: Yoshihiro Aoyama, Kyoto (JP); Junichi Kita, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/887,565

(22) Filed: Jun. 25, 2001

(65) Prior Publication Data

US 2002/0002857 A1 Jan. 10, 2002

(30) Foreign Application Priority Data

Jul. 3, 2000 (JP) ........................... 2000-200537

(51) Int. Cl.[7] ................ G01N 33/497; G01N 33/48; G01N 7/00; C12Q 1/00
(52) U.S. Cl. .............. 73/23.34; 73/23.41; 73/23.42; 422/88
(58) Field of Search ................... 73/23.34, 31.07, 73/31.03, 31.05, 23.35, 23.41–23.42; 422/88

(56) References Cited

U.S. PATENT DOCUMENTS

| | | | |
|---|---|---|---|
| 5,313,821 A | * 5/1994 | Bett et al. ................... 73/23.34 |
| 5,801,297 A | * 9/1998 | Mifsud et al. ............... 73/23.34 |
| 5,970,804 A | * 10/1999 | Robbat, Jr. ................ 73/863.12 |
| 5,996,396 A | * 12/1999 | Marshall et al. ............. 73/23.34 |
| 6,006,583 A | * 12/1999 | Hayashi ...................... 73/23.34 |
| 6,244,096 B1 | * 6/2001 | Lewis et al. .................. 73/23.2 |
| 6,360,584 B1 | * 3/2002 | Okubo et al. ............... 73/23.34 |
| 6,374,662 B1 | * 4/2002 | Oda et al. ................... 73/23.34 |

* cited by examiner

Primary Examiner—Hezron Williams
Assistant Examiner—David J. Wiggins
(74) Attorney, Agent, or Firm—Kanesaka & Takeuchi

(57) ABSTRACT

A sample gas is introduced into a collecting pipe filled with a collecting agent to collect odor components therein, and a gas, such as nitrogen gas, is introduced into the collecting pipe to remove moisture and so on. Then, a heater is heated to raise a temperature of the collecting pipe so that a part of the odor components adsorbed by the collecting agent is separated therefrom, and then, a carrier gas is supplied to the collecting pipe to send the separated odor components to a sensor. After a predetermined time has passed, the heater is further heated to send the separated odor components to the sensor. The heater may be further increased. Thus, an output information of the gas sensor in one cycle of measurement can be increased.

6 Claims, 4 Drawing Sheets

ODOR IDENTIFYING APPARATUS

BACKGROUND OF THE INVENTION AND RELATED ART STATEMENT

The present invention relates to an odor identifying apparatus for identifying an odor component in a sample gas provided with one or a plurality of gas sensors.

The odor identifying apparatus of this type is used for obtaining odor intensity and odor quality in research and development fields relating to odors, flavors or fragrances (hereinafter simply referred to as "odor") of foods and perfumes; in quality control fields relating to odors of foods and production of chemical products; and in control or management fields of an odor environment.

Heretofore, measurement of the odor has mainly been made through a component analysis using a gas chromatograph/mass spectrometry (hereinafter referred to as "GC/MS"). However, there have been various defects such that the component analysis using the GC/MS takes a long time; skills and experiences are required; it is difficult to analyze and interpret too much output information relating to a sample; and it is very difficult to obtain a correlation with a sensory or organoleptic value of the odor.

Thus, there has been proposed an odor identifying apparatus using a gas sensor wherein the above-described defects are solved. As a gas sensor to be used in the odor identifying apparatus, there are mentioned an oxide semiconductor sensor, electrically conductive high polymer sensor, a sensor wherein a gas absorption film is formed on a surface of a quartz oscillator, i.e. quartz crystal microbalance (hereinafter referred to "QCM"), and a sensor wherein a gas adsorption film is formed on a surface of a surface acoustic wave (hereinafter referred to "SAW") device. In the oxide semiconductor sensor, there is used a phenomenon wherein an electric resistance of the oxide semiconductor is changed by an oxidation reduction reaction of gas components in a sample gas. In the electrically conductive high polymer sensor, there is used a phenomenon wherein a conductance of an electrically conductive high polymer is changed by adsorption of the gas components. In QCM and SAW device, there is used a phenomenon wherein a frequency is changed according to a weight change when the gas components are adsorbed by the gas adsorption film.

In the odor identifying apparatus for measuring the odor components in the sample gas by using the above-described phenomena, there is provided one or a plurality of gas sensors having different response characteristics with respect to the odor components, wherein a signal detected by the gas sensor is displayed as it is, or signals detected by the plural gas sensors are subjected to a multivariate analysis. In other words, the odor components in the sample gas are measured by applying a technique what is called chemometrics.

There is an odor identifying apparatus including a collecting portion filled with a collecting agent for absorbing odor components in a sample gas. In the odor identifying apparatus, the sample gas is introduced into the collecting portion to allow the collecting agent to absorb the odor components; a drying gas, such as a nitrogen gas, is introduced into the collecting portion to dry the circumference of the odor components; the collecting portion is heated to separate the odor components absorbed by the collecting agent; and a carrier gas is supplied to the collecting portion at a predetermined flow rate, so that the odor components are guided to the gas sensor by the carrier gas for measurement.

In the odor identifying apparatus using the gas sensor, an output for one sample gas in one measurement is one kind with respect to one gas sensor. Therefore, there is a problem such that when compared with the GC/MS, information quantity is very small.

Therefore, in view of the above problems, the present invention has been made and an object of the invention is to provide an odor identifying apparatus, wherein a quantity of output information relating to a plurality of sensors in one measurement can be increased.

Further objects and advantages of the invention will be apparent from the following description of the invention.

SUMMARY OF THE INVENTION

An odor identifying apparatus of the invention comprises one or a plurality of gas sensors, a collecting portion filled with a collecting agent for absorbing odor components in a sample gas, a sample gas introducing portion for introducing the sample gas into the collecting portion, a heating portion for heating the collecting portion to separate the odor components absorbed by the collecting agent, and a carrier gas supply portion for supplying a carrier gas to the collecting portion to supply the separated odor components to the gas sensors. The odor identifying apparatus further comprises an expelling condition control portion for changing at least a part of an expelling condition in time sequence in one cycle of the measurement when the odor components adsorbed by the collecting agent in the collecting portion are separated.

One example in changing the expelling condition in time sequence in one cycle of the measurement is a heating temperature at the heating portion in the collecting portion.

When the odor components adsorbed by the collecting agent in the collecting portion are separated by the expelling condition control portion, the heating temperature of the collecting portion is changed stepwise from a low temperature to a high temperature. Thus, outputs of the gas sensor at the respective stages of the expelling conditions can be obtained, so that a plurality of outputs for each gas sensor can be obtained in one cycle of the measurement.

Further, in the invention, one of the expelling conditions may only be performed in one measurement. Namely, one of the heating conditions, such as from 40 to 100° C., 100 to 150° C., 150 to 250° C., is selected, and the odor components at the particular temperature are obtained.

Another example for changing the expelling condition in time sequence in one cycle of the measurement is a supply flow rate of the carrier gas to the collecting portion from the carrier gas supply portion.

When the odor components adsorbed by the collecting agent in the collecting portion are separated therefrom by the expelling condition control portion, the supply flow rate of the carrier gas to the collecting portion is changed stepwise from a small flow rate to a large flow rate. Thus, the outputs of each gas sensor at the respective stages of the expelling conditions can be obtained, so that a plurality of outputs for each gas sensor can be obtained in one cycle of the measurement.

DETAILED DESCRIPTION OF THE PREFERRED EMBODIMENT

Figure 1:
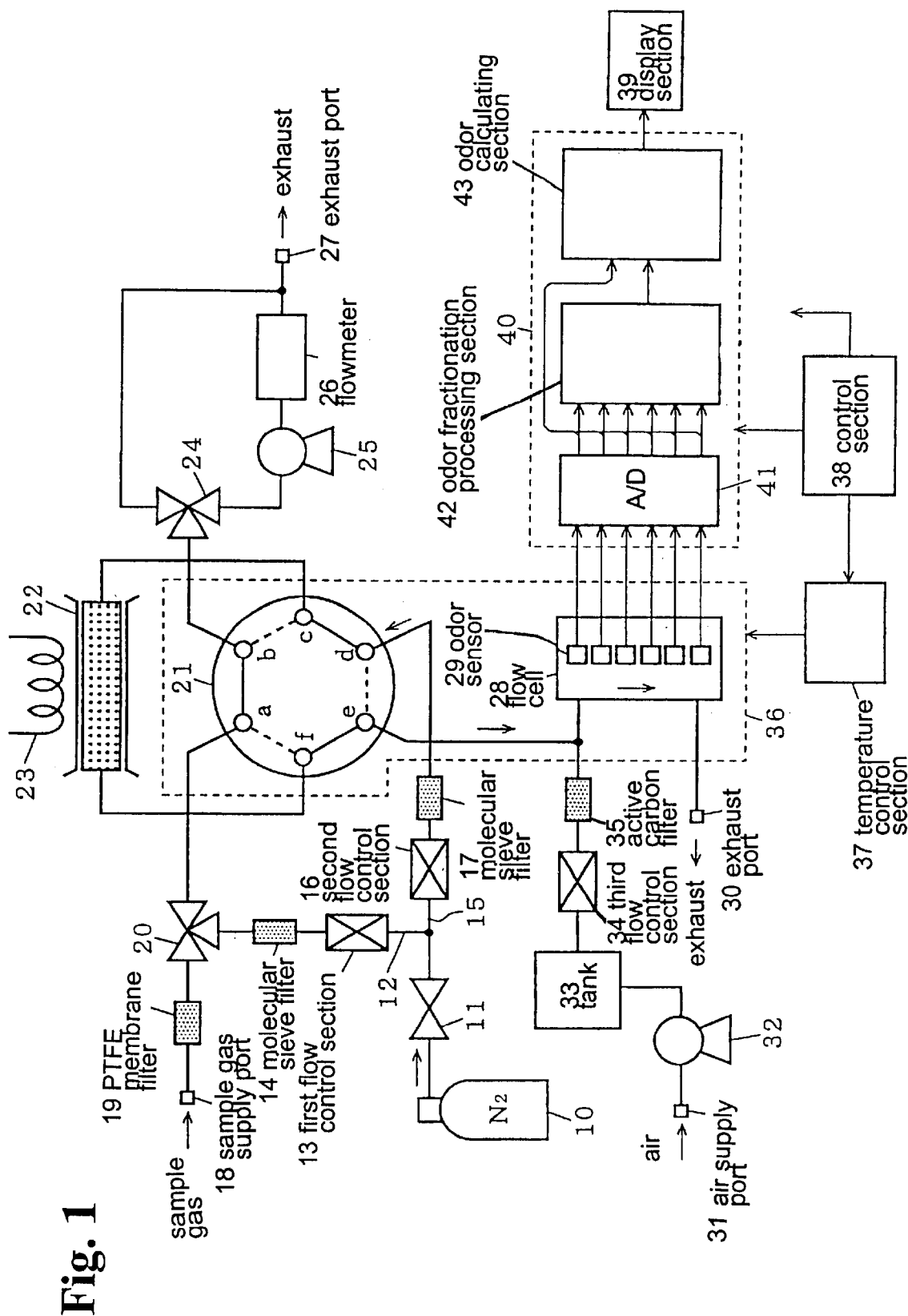
FIG. 1 is a detailed structure showing an order measuring apparatus as an embodiment of the invention.

Hereinafter, an embodiment of the odor measuring apparatus according to the present invention will be explained with reference to the attached drawings. FIG. 1 is a detailed structure of the odor measuring apparatus, which is shown on the basis of gas passages.

In FIG. 1, a gas outlet of a nitrogen gas container 10 filled with pure nitrogen gas ($N_2$) is attached to a constant pressure valve 11, and an outlet of the valve 11 is branched into first and second passages 12 and 15. Namely, the first nitrogen gas passage 12 has a first flow control section 13, such as a mass flow controller, and a molecular sieve filter 14 for removing impurities, and the second nitrogen gas passage 15 has a second flow control section 16, such as a mass flow controller, and a molecular sieve filter 17 for removing impurities. A sample gas passage, which is connected to a sample gas supply port 18 through a PTFE (polytetrafluoroethylene) membrane filter 19 for removing dusts, and the first nitrogen gas passage 12 are selectively connected to a port a of a six-way or hexagonal valve (six-port and two-position valve) 21 through a three-way valve 20. Also, the second nitrogen gas passage 15 is connected to a port d of the six-way valve 21. A collecting tube 22 provided with a heater for heating is connected between a port c and a port f of the six-way valve 21. The collecting tube 22 is filled with, for example, a carbon adsorbent, or other appropriate adsorbent in accordance with the odor components of the measurement object.

The port b of the six-way valve 21 is selectively connected by a three way valve 24 to either a passage passing through a pump 25 and a flowmeter 26 or a passage not passing through these members, and either of the passages leads to an exhaust port 27. A port e of the six-way valve 21 is connected to a flow cell 28 in which a plurality of odor sensors 29 (six odor sensors in the embodiment) is disposed, and a downstream side outlet of the flow cell 28 is connected to an exhaust port 30. The odor sensors 29 are sensors using metal oxide semiconductors as sensitive films, which have characteristics different in detection sensitivities with respect to various kinds of odor components, respectively. The six-way valve 21 and the flow cell 28 are disposed inside a thermostat tank 36, a temperature of which is controllable at a predetermined temperature by a temperature control section 37.

In a tank 33, air sucked from an air supply port 31 by a pump 32 is compressed and stored, and an outlet of the tank 33 is connected to an inlet of the flow cell 28 through a third flow control section 34 and an active carbon filter 35 for removing impurities. Accordingly, an adequate amount of air can be mixed with a sample gas flowing into the flow cell 28. Incidentally, it can be structured that a pure oxygen gas may be mixed instead of air. If the pure oxygen gas is used, a volume thereof mixing with the sample gas can be extremely reduced as compared with the case using air, so that the ratio of diluting the odor components is small to be advantageous in improving the sensitivity of the detection by the odor sensor 29.

Detection signals from the six odor sensors 29 are inputted in parallel into a signal processing section 40. The signal processing section 40 includes an analog-to-digital converter 41 for converting an analog detection value of each odor sensor 29 into a digital value, an odor fractionation processing section 42, and an odor index calculating section 43. The odor fractionation processing section 42 and the odor index calculating section 43 can be made by executing a predetermined software in, for example, a personal computer. The odor index calculated at the signal processing section 40 is displayed at a display section 39. Also, a control section 38 has a function of controlling the three-way valves 20 and 24, the six-way valve 21, the pumps 25 and 32, the heater 23, the temperature control section 37, and the signal processing section 40 or the like as described later in accordance with a predetermined program.

Incidentally, although the metal oxide semiconductor sensors are used as the odor sensors 29 in the present embodiment, the odor sensors 29 are not limited thereto, and sensors utilizing conductive high polymers can be used as the odor sensors 29. In this case, since there is no need to supply air or oxygen to the flow cell 28, in the structure shown in FIG. 1, the structure for mixing air with the gas flowing into the flow cell 28 can be omitted.

Next, operations in case of obtaining the detection signals by the odor sensors 29 in the odor measuring apparatus will be explained.

Collecting Odor Components

Firstly, the control section 38 switches the three-way valve 20 such that the sample gas supply port 18 and the port a of the six-way valve 21 are connected, and at the same time, the control section 38 switches the three-way valve 24 such that the port b of the six-way valve 21 is connected to the pump 25. Also, the six-way valve 21 is switched to become a connection condition shown by broken lines in FIG. 1, and the pump 25 is actuated. Accordingly, a relatively large solid suspended material, such as dust, contained in the sample gas sucked from the sample gas supply port 18 by a suction force of the pump 25 is removed from the sample gas by the membrane filter 19, and the sample gas is introduced into the collecting tube 22 through the three-way valve 20 and the six-way valve 21 (in a left to right direction in FIG. 1). Further, the sample gas passes through the six-way valve 21, the three-way valve 24, the pump 25 and the flowmeter 26, and is discharged from the exhaust port 27. At this time, heating by the heater 23 is not carried out.

When the sample gas passes through the collecting tube 22 as described above, odor components contained in the sample gas are adsorbed by the adsorbent. In the present embodiment, the control section 38 controls the suction force of the pump 25 such that the detection value by the flowmeter 26 becomes a predetermined constant value, and flowing time of the sample gas becomes a predetermined value.

Replacement of the Gas in the Collecting Tube

When the flowing time has elapsed, the control section 38 switches the three-way valve 20 to connect the first nitrogen gas passage 12 with the port a of the six-way valve 21, and at the same time, the control section 38 switches the three-valve 24 to connect the port b of the six-way valve 21 directly with the exhaust port 27. Accordingly, instead of the sample gas, the nitrogen gas supplied from the nitrogen gas container 10 passes through the first nitrogen gas passage 12, the three-way valve 20, the six-way valve 21, the collecting tube 22, the six-way valve 21, and the three-way valve 24, and is discharged from the exhaust port 27. As a result, the sample gas remained in the passages or flowing route including the collecting tube 22 is pushed to an outside by the nitrogen gas. At this time, since the heating by the heater 23 is not carried out, the odor components adsorbed by the adsorbent earlier remain as they are. On the other hand, since the nitrogen gas is extremely dry, most of water adsorbed to the adsorbent and moisture adhering to the inner walls of the passages are vaporized into the nitrogen gas and carried away to the outside, so that dehumidification to the certain extent can be achieved.

Introduction of the Odor Components Into the Odor Sensors

After the nitrogen gas flows through the collecting tube 22 for an adequate time, and the control section 38 switches the six-way valve 21 to become a connection condition shown by the solid lines in FIG. 1. Then, there is formed a flowing route comprising the second nitrogen gas passage 15, the six-way valve 21, the collecting tube 22, the six-way valve 21, the flow cell 28, and the exhaust port 30. In this condition, the heater 23 is energized, and the collecting tube 22 is heated rapidly, for example, at the temperature rising speed of approximately 10° C./second. As a result, the odor components adsorbed to the adsorbent in the collecting tube 22 are released from the adsorbent, and are carried to the flow cell 28 by the nitrogen gas flowing in the direction opposite to the direction flowing before, i.e. right to left in FIG. 1.

Air stored. in the tank 33 is adjusted to have an adequate flow rate by the third flow control section 34, and after the undesired components causing a disturbance of the measurement is removed by the active carbon filter 35, air is mixed with the measurement gas flowing into the flow cell 28. Since air contains the oxygen gas, the oxygen gas together with the odor components flow into the flow cell 28, and the oxygen gas moleculars are adsorbed by sensitive films formed of metal oxide semiconductors, so that an oxidation reduction reaction occurs between the oxygen gas moleculars and the moleculars of the odor components. Accordingly, conductivities of the odor sensors 29 are changed, and electric resistance between electrodes thereof is changed. The detection signals due to the resistance change are sent to the signal processing section 40.

During the measurement as described above, the six-way valve 21, the flow cell 28 and the passage connecting therebetween are maintained at a fixed temperature, for example, about 40° C., which is slightly higher than the room temperature. As a result, the effect to the odor sensors 29 due to the change of the ambient temperature can be decreased, and it can be prevented that the stability of the detection sensitivity is deteriorated due to adhesion of the high boiling compounds to the inner wall of the passages.

Cleaning the Odor Sensors

When the odor components adsorbed to the adsorbent in the collecting tube 22 are sufficiently released, the control section 38 switches the six-way valve 21 again to become the connection condition shown by the broken lines in FIG. 1, and the temperature in the tank 36 is increased by the temperature control section 37 to a predetermined temperature. Accordingly, the clean nitrogen gas flows through the flow cell 28. When the temperatures of the odor sensors 29 rise, the odor components or other impurities adsorbed to the sensitive films of the odor sensors 29 can be easily released, and exhausted from the exhaust port 30 by being carried on the nitrogen gas. As a result, the sensitive films of the odor sensors 29 are recovered, and return to the condition capable of detecting the odor components again.

Figure 2:
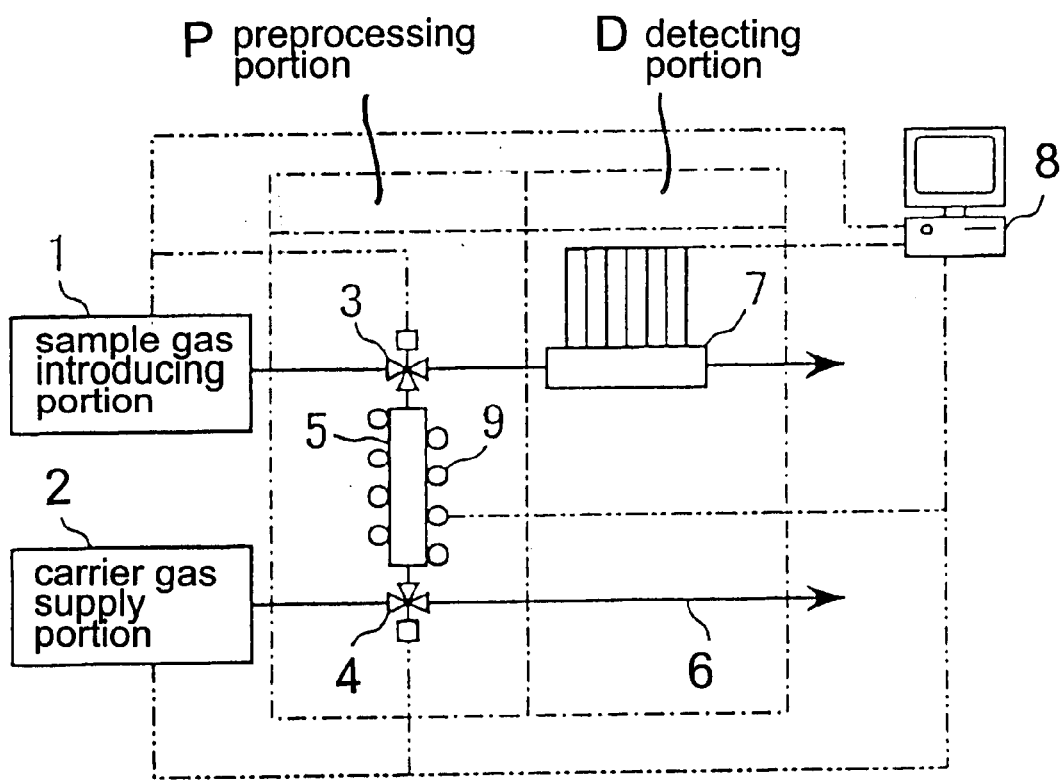
FIG. 2 is a diagram showing a basic structure of an embodiment of an odor identifying apparatus according to the invention.

FIG. 2 is a diagram showing a general structure of an embodiment according to the invention.

An odor identifying apparatus of the present invention includes a sample gas introducing portion 1 for introducing a sample gas. The sample gas introducing portion 1 supplies also a dry nitrogen gas or inert gas in addition to the sample gas. A passage from the sample gas introducing portion 1 is connected to a three-way electromagnetic valve 3. The valve 3 is also connected to a passage extending to one end side of a collecting pipe, i.e. collecting portion, 5 filled with a collecting agent for absorbing odor components in the sample gas, and a passage extending to six oxide semiconductor sensors, i.e. gas sensors, 7 having different response characteristics. The valve 3 changes by shifting the passage extending to the collecting pipe 5 to the passage extending to the sample gas introducing portion 1 or the passage extending to the sensors 7.

A heater, i.e. heating portion, 9 is provided around the collecting pipe 5 to heat the same for separating the odor components adsorbed by the collecting agent filled in the collecting pipe 5.

The other end side opposite to the valve 3 of the collecting pipe 5 is connected to a three-way electromagnetic valve 4. The valve 4 is also connected to a passage extending to a carrier gas supply portion 2 for supplying the dry nitrogen gas, i.e. carrier gas, to the collecting portion 5 in order to supply the odor components separated in the collecting pipe 5 to the sensors 7, and to a discharge passage 6. The valve 4 connects by switching the passage communicating with the collecting pipe 5 to the passage communicating with the carrier gas supply portion 2 or to the discharge passage 6.

The valves 3 and 4, collecting pipe 5 and heater 9 constitute a pre-processing portion P, and the six sensors 7 constitute a detecting portion D.

The sample gas introducing portion 1, valves 3 and 4, heater 9 and carrier gas supply portion 2 are electrically connected to a personal computer (hereinafter referred to as "PC") 8, and operations thereof are controlled by the PC 8. The sensors 7 are also electrically connected to the PC 8, and outputs from the sensors 7 are sent to the PC 8 to be processed thereat.

An expelling control portion of the present invention is formed by the PC 8.

Figure 3:
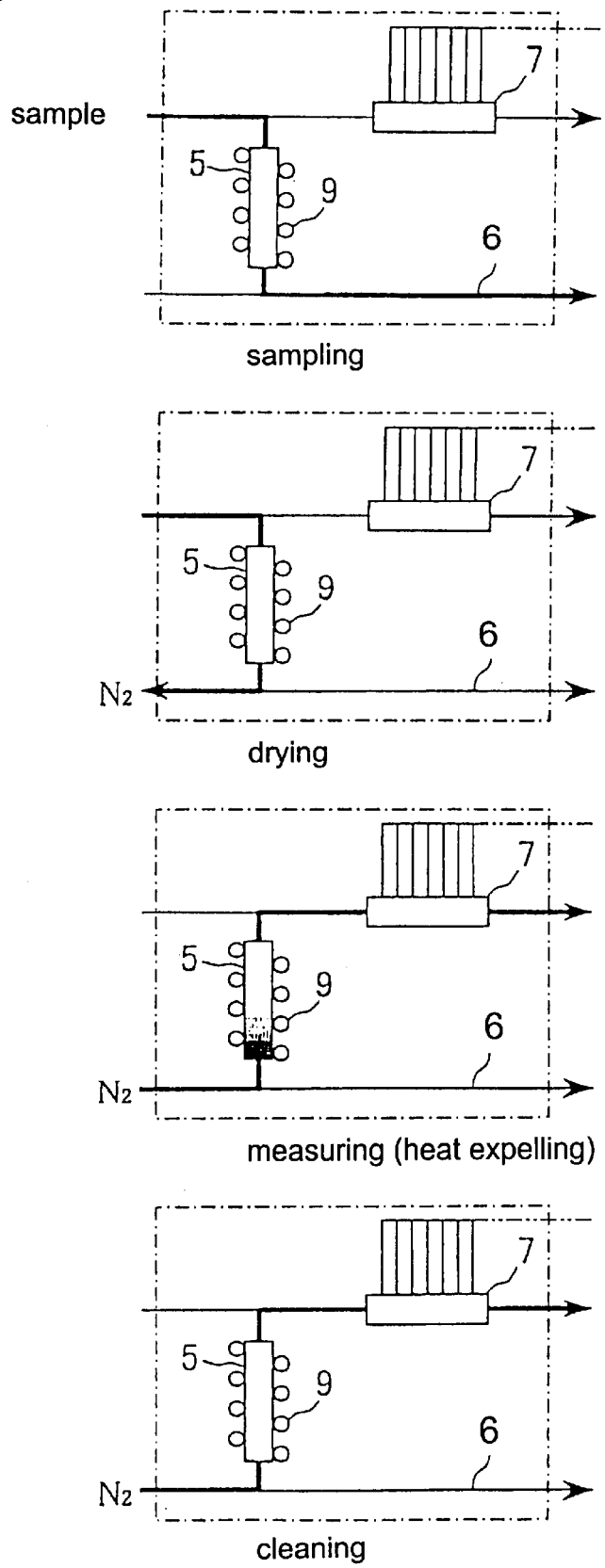
FIGS. 3. is a flow chart showing a measuring process of the embodiment according to the invention.

FIG. 3 is a flow chart showing a measuring process of an embodiment of the invention, wherein thick lines represent passages through which the gas is flowing. In FIG. 3, the sample introducing portion 1, valves 3, 4 and carrier gas supply portion 2 are omitted. With reference to FIG. 2 and FIG. 3, operations of the embodiment are explained.

Sampling Process

The passage connected to the collecting pipe 5 is switched to the passage leading to the sample gas introducing portion 1 by the valve 3. The passage connected to the collecting pipe 5 is switched to the discharge passage 6 by the valve 4. The collecting pipe 5 is held at, for example, the room temperature without using the heater 9. The sample gas is supplied to the collecting pipe 5 from the sample gas introducing portion 1 through the valve 3. Odor components in the sample gas are adsorbed by the collecting agent filled in the collecting pipe 5 to be collected therein. The sample gas passing through the collecting pipe 5 is discharged through the valve 11 and the discharge passage 6.

Drying Process

The passage connected to the collecting pipe 5 is connected to the carrier gas supply portion 2 by switching the valve 4. A nitrogen gas or $N_2$ is supplied to the collecting pipe 5 from the sample gas introducing portion 1 through the valve 3. Moisture and interfering components contained in the sample gas and present in the collecting pipe 5 are discharged together with the nitrogen gas through the valve 4 and the carrier gas supply portion 2, so that the moisture and interfering components are removed from the collecting pipe 5. Since the influence of the moisture is removed with respect to outputs of the sensors 7 through the drying process, a repeatability or accuracy of the measurements can be improved.

Measuring (Heat Expelling) Process

The passage connected to the collecting pipe 5 is connected to the sensors 7 by switching the valve 3.

The heater 9 is heated, and a temperature of the collecting pipe 5 is raised to 100° C. A part of the odor components adsorbed by the collecting agent in the collecting pipe 5 is separated from the collecting agent. The nitrogen gas is supplied to the collecting pipe 5 through the valve 4 at a predetermined flow rate from the carrier gas supply portion 2. The odor components separated from the collecting agent are sent to the sensors 7 together with the nitrogen gas through the valve 3. The six oxide semiconductor sensors detect the odor components, respectively, and the outputs thereof are sent to the PC 8.

After a predetermined time has passed, the heater 9 is further heated to raise the temperature of the collecting pipe 5 to 150° C. Parts of the odor components remaining in the collecting pipe are separated from the collecting agent. Since the nitrogen gas has been supplied to the collecting pipe 5 from the carrier gas supply portion 13 at a predetermined flow rate, the odor components separated from the collecting agent are sent to the sensors 7 together with the nitrogen gas through the valve 3. The six oxide semiconductor sensors detect the odor components, respectively, and the outputs thereof are sent to the PC 8.

After a further predetermined time has passed, the heater 9 is further heated to raise the temperature of the collecting pipe 5 to 250° C. The odor components remaining in the collecting pipe 5 are separated from the collecting agent. Since the nitrogen gas has been supplied to the collecting pipe 5 from the carrier gas supply portion 2 at a predetermined flow rate, the odor components separated from the collecting agent are sent to the sensors 7 together with the nitrogen gas through the valve 3. The six oxide semiconductor sensors detect the odor components, respectively, and outputs thereof are sent to the PC 8.

In the measuring process, with respect to a quantity of the sample gas introduced into the collecting pipe 5 in the sampling process, the nitrogen gas flow rate to be supplied to the collecting pipe 5 from the carrier gas supply portion 2 is controlled. Thus, while the odor components are concentrated or diluted, the odor components are supplied to the sensors 7.

Cleaning Process

While supplying the nitrogen gas to the collecting pipe 5 from the carrier gas supply portion 2, the heater 9 is heated to further raise the temperature of the collecting pipe 5. Thus, the odor components remaining in the collecting pipe 5 can be removed. Thereafter, heating of the heater 9 is stopped, and after the collecting pipe 5 is cooled down, supply of the nitrogen gas from the carrier gas supply portion 2 is stopped. The valves 3, 4 are switched to return to the initial condition of the measurement, i.e. sampling condition.

Figure 4A:
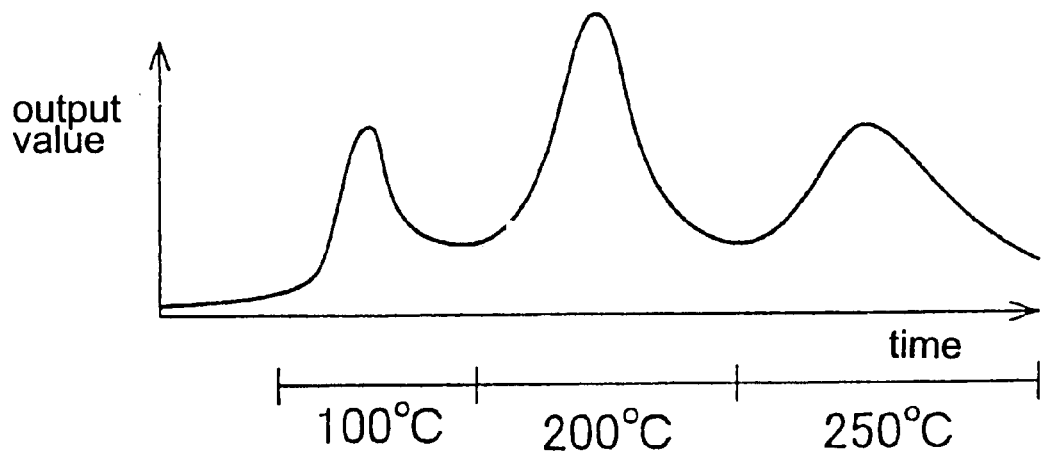
FIG. 4(A) is a waveform diagram showing an output of an oxide semiconductor sensor obtained in the measuring process of a sample gas according to the invention.
Figure 4B:
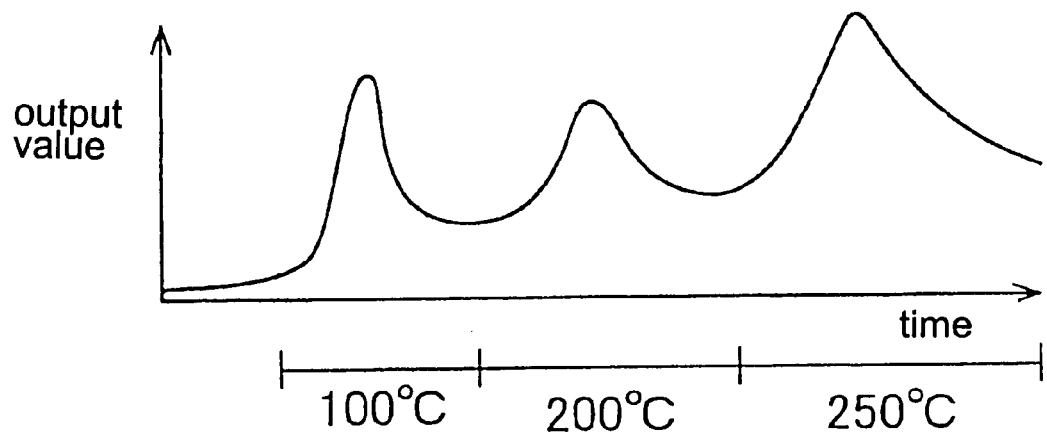
FIG. 4(B) is a waveform diagram showing an output of an oxide semiconductor sensor obtained in the measuring process of another sample gas having an odor different from that of FIG. 4(A) according to the invention.

FIGS. 4(A) and 4(B) are waveforms for showing outputs of the oxide semiconductor sensors obtained in the measuring process, respectively, wherein samples having different odors were measured. The ordinate represents output values, and the abscissa represents time.

As shown in FIGS. 4(A) and 4(B), in case the heating temperatures of the collecting pipe are changed stepwise, such as 100° C., 150° C. and 250° C., in one cycle of the measurement, odor components separated at 100° C., odor components separated at 150° C. and odor components separated at 250° C. are detected separately based on adsorption strengths peculiar to the respective odor components.

As can be seen from FIGS. 4(A) and 4(B), since the samples having different odors have different structures and concentrations of the odor components, outputs of the gas sensors at the respective temperatures are different. Therefore, an output information quantity with respect to each gas sensor in the one cycle of the measurement can be increased. With the increased output information quantity of the gas sensor, reliability of the analyzing results for the odor identification can be improved.

In the above embodiment, the odor components are separated stepwise from the collecting agent by stepwise raising of the heating temperature of the collecting pipe in one cycle of the measurement. However, the present invention is not limited thereto, and when the odor components absorbed by the collecting agent in the collecting portion are separated therefrom, the flow rate of supplying the carrier gas to the collecting portion from the carrier gas supply portion may be increased stepwise while holding the heating temperature of the collecting pipe constant. Since the quantities of the odor components to be separated per unit time are also increased when the flow rates of the carrier gas are increased, the outputs of the gas sensors can be obtained at the respective stages of the flow rates of the carrier gas. Thus, a quantity of the output information with respect to each gas sensor in one cycle of the measurement can be increased.

Also, both the heating temperature of the collecting pipe and the supply flow rate of the carrier gas in one cycle of the measurement may be changed stepwise.

In the above embodiment, while the odor identifying apparatus using the metal oxide semiconductor sensors is applied to the invention, the present invention is not limited thereto. An odor identifying apparatus using an electrically conductive high polymer sensor, or a sensor obtained by forming a gas adsorption film on a surface of a quartz crystal microbalance or on a surface of a surface acoustic wave, i.e. SAW, device may be applied to the invention.

Also, in the above embodiment, one collecting pipe is provided as the collecting portion, but a plurality of collecting pipes having different collecting characteristics may be provided.

In the odor identifying apparatus according to the invention, when the odor components adsorbed by the collecting agent in the collecting portion are separated by the expelling condition control portion, since at least a part of the expelling conditions is changed in time sequence in one cycle of the measurement, the outputs of the gas sensor at the respective stages of the expelling conditions can be obtained. Thus, a plurality of the outputs in each gas sensor in one cycle of the measurement can be obtained.

While the invention has been explained with reference to the specific embodiments of the invention, the explanation is illustrative and the invention is limited only by the appended claims.

What is claimed is:

1. An odor identifying apparatus comprising:
    at least one gas sensor for sensing an odor,
    a collecting portion connected to the at least one gas sensor and having a collecting agent for absorbing odor components in a sample gas,
    a sample gas introducing portion connected to the collecting portion for introducing the sample gas into the collecting portion, a heating portion for heating the collecting portion to separate the odor components absorbed in the collecting agent, a carrier gas supply portion connected to the collecting portion for supplying a carrier gas to the collecting portion to provide the odor components absorbed in the collecting agent to the at least one gas sensor, and a control portion electrically connected to at least one of the heating portion and the carrier gas supply portion for controlling the same so that an expelling condition of the odor components absorbed in the collecting agent is changed sequentially in one cycle of measurement by the at least one gas sensor.

2. An odor identifying apparatus as claimed in claim 1, wherein the expelling condition to be changed in the measurement is a temperature at the heating portion such that the temperature in the heating portion is changed in one cycle of the measurement.

3. An odor identifying apparatus as claimed in claim 1, wherein the expelling condition to be changed in the measurement is a supply flow rate of the carrier gas to the collecting portion from the carrier gas supply portion.

4. An odor identifying apparatus comprising:

at least one gas sensor for sensing an odor, a collecting portion connected to the at least one gas sensor and having a collecting agent for absorbing odor components in a sample gas, a sample gas introducing portion connected to the collecting portion for introducing the sample gas into the collecting portion, a heating portion for heating the collecting portion to separate the odor components absorbed in the collecting agent, a carrier gas supply portion connected to the collecting portion for supplying a carrier gas to the collecting portion to provide the odor components absorbed in the collecting agent to the at least one gas sensor, and a control portion electrically connected to at least one of the heating portion and the carrier gas supply portion for controlling the same so that an expelling condition of the odor components absorbed in the collecting agent is changed sequentially in one cycle of measurement by the at least one gas sensor, said expelling condition to be changed in the measurement being a temperature at the heating portion, which is heated stepwise to increase the temperature such that the temperature in the heating portion is changed in said one cycle of the measurement.

5. An odor identifying apparatus comprising:

at least one gas sensor for sensing an odor, a collecting portion connected to the at least one gas sensor and having a collecting agent for absorbing odor components in a sample gas, a sample gas introducing portion connected to the collecting portion for introducing the sample gas into the collecting portion, a heating portion for heating the collecting portion to separate the odor components absorbed in the collecting agent, a carrier gas supply portion connected to the collecting portion for supplying a carrier gas to the collecting portion to provide the odor components absorbed in the collecting agent to the at least one gas sensor, and a control portion electrically connected to at least one of the heating portion and the carrier gas supply portion for controlling the same so that an expelling condition of the odor components absorbed in the collecting agent is changed sequentially in one cycle of measurement by the at least one gas sensor, said expelling condition to be changed in the measurement being a supply flow rate of the carrier gas, which is increased stepwise, to the collecting portion from the carrier gas supply portion.

6. An odor identifying apparatus as claimed in claim 5, wherein said control portion controls such that after the sample gas passes through the collecting portion for collecting the odor components in the collecting agent, a gas flows through the collecting portion to remove components other than the odor components without heating the heating portion, and then the expelling condition is changed to start the measurement.

* * * * *